(12) United States Patent
Tsuji et al.

(10) Patent No.: US 11,059,059 B2
(45) Date of Patent: Jul. 13, 2021

(54) ELECTROSTATIC ATOMIZING APPARATUS AND ELECTRICALLY-CHARGED WATER PARTICLE SPRAYING APPARATUS

(71) Applicant: HOCHIKI CORPORATION, Tokyo (JP)

(72) Inventors: Toshihide Tsuji, Tokyo (JP); Tetsuo Yoshida, Tokyo (JP)

(73) Assignee: HOCHIKI CORPORATION, Tokyo (JP)

( * ) Notice: Subject to any disclaimer, the term of this patent is extended or adjusted under 35 U.S.C. 154(b) by 50 days.

(21) Appl. No.: 16/247,889

(22) Filed: Jan. 15, 2019

(65) Prior Publication Data

US 2019/0176172 A1   Jun. 13, 2019

Related U.S. Application Data

(63) Continuation of application No. PCT/JP2017/024799, filed on Jul. 6, 2017.

(30) Foreign Application Priority Data

Jul. 21, 2016 (JP) .............................. JP2016-143136
Apr. 24, 2017 (JP) .............................. JP2017-085016

(51) Int. Cl.
 *B05B 5/053* (2006.01)
 *B08B 15/00* (2006.01)
 (Continued)

(52) U.S. Cl.
 CPC .............. *B05B 5/0535* (2013.01); *B03C 3/00* (2013.01); *B08B 15/00* (2013.01); *A61L 9/14* (2013.01);
 (Continued)

(58) Field of Classification Search
 CPC ..... B05B 5/0533; B05B 5/0535; A62C 31/02; A61L 9/14; F24F 1/00; F24F 1/02; B08B 15/00
 See application file for complete search history.

(56) References Cited

U.S. PATENT DOCUMENTS 3,774,844 A * 11/1973 Walberg ................... B05B 5/03
 239/695
4,347,984 A *  9/1982 Sickles .................. B05B 5/043
 239/291
(Continued)

FOREIGN PATENT DOCUMENTS

DE      25 14 117      10/1975
JP    2001-332398     11/2001
(Continued)

OTHER PUBLICATIONS

Supplementary European Search Report dated Feb. 19, 2020 in corresponding European Patent Application No. 17830858.1.
(Continued)

*Primary Examiner* — Alex M Valvis
(74) *Attorney, Agent, or Firm* — Wenderoth, Lind & Ponack, L.L.P.

(57) ABSTRACT

An electrostatic atomizing apparatus includes: a liquid nozzle portion for releasing a liquid column into an open space; a liquid conduit portion for introducing pressurized liquid into the liquid nozzle portion; a liquid-side electrode disposed inside the liquid conduit portion for coming into contact with the pressurized liquid; a gas conduit portion made of an insulation material and having a gas nozzle portion disposed around the liquid nozzle portion for converting the liquid column into fine particles to generate an atomized stream by making a gas stream from the gas nozzle portion act at an atomization point of the liquid column released into the open space from the liquid nozzle portion; and a ring-shaped induction electrode disposed around the atomization point located in the open space and having an electrode conductor made of a conductive material and coated with an insulation material.

4 Claims, 7 Drawing Sheets

(51) Int. Cl.
    *B03C 3/00*     (2006.01)
    *A62C 31/02*     (2006.01)
    *A61L 9/14*     (2006.01)
    *F24F 1/02*     (2019.01)
    *B01D 47/06*     (2006.01)

(52) U.S. Cl.
    CPC .............. *A62C 31/02* (2013.01); *B01D 47/06* (2013.01); *F24F 1/02* (2013.01)

(56) References Cited

U.S. PATENT DOCUMENTS

| | | | | |
|---|---|---|---|---|
| 5,044,564 A * | 9/1991 | Sickles | ................. | B05B 5/0533 |
| | | | | 239/690.1 |
| 5,584,931 A * | 12/1996 | Buhlmann | .............. | B05B 5/032 |
| | | | | 118/300 |
| 6,474,573 B1 * | 11/2002 | Kelly | ................... | B05B 5/0255 |
| | | | | 239/690 |
| 7,105,058 B1 * | 9/2006 | Sinyagin | ................. | D04H 3/02 |
| | | | | 118/713 |
| 7,748,651 B2 * | 7/2010 | Amari | ................... | B05B 5/043 |
| | | | | 239/690 |
| 2003/0001031 A1 * | 1/2003 | Heldt | ....................... | B05B 5/04 |
| | | | | 239/700 |
| 2013/0180737 A1 | 7/2013 | Tsuji et al. | | |

FOREIGN PATENT DOCUMENTS

| | | |
|---|---|---|
| JP | 2008-130643 | 6/2008 |
| JP | 2009-103335 | 5/2009 |
| JP | 2009-106405 | 5/2009 |
| JP | 2013-226518 | 11/2013 |
| WO | 2013/161476 | 10/2013 |

OTHER PUBLICATIONS

Machine Translation of JP 2008-130643 issued Nov. 30, 2001.
Machine Translation of WO 2013/161476 issued Oct. 21, 2013.
International Search Report dated Oct. 3, 2017 in International (PCT) Application No. PCT/JP2017/024799.

* cited by examiner

ELECTROSTATIC ATOMIZING APPARATUS AND ELECTRICALLY-CHARGED WATER PARTICLE SPRAYING APPARATUS

BACKGROUND OF THE INVENTION

1. Technical Field

The present invention relates to an electrostatic atomizing apparatus and an electrically-charged water particle spraying apparatus for electrically charging and releasing fine particles of liquid such as water, seawater, or a chemical solution.

2. Description of the Related Art

Conventionally, an electrostatic atomizing apparatus for electrically charging and releasing fine particles of liquid such as water is provided with an induction electrode portion disposed near an injection space of an injection nozzle, and a water-side electrode portion disposed inside the injection nozzle and coming into contact with a water-type fire extinguishing agent, and injected particles are electrically charged by applying an external electric field generated by applying voltage between the induction electrode portion and the water-side electrode portion via a power supply to the water-type extinguishing agent being in the process of injection performed by the injection nozzle.

According to such an electrostatic atomizing apparatus, fine particles having an average particle diameter of 20 to 200 micrometers can be released, and, for example, when the apparatus is used in water mist extinguishing equipment, by electrically charging water particles sprayed from an electrically-charging spray head, Coulomb force causes not only adhesion of the water particles to a high-temperature burning surface but also adhesion of the water particles to every single surface of a burning material, and therefore, as compared with electrically-uncharged normal water particles, a wetting effect can be significantly enhanced so that fire extinguishing power can be increased.

In addition, when the apparatus is used in water atomization cooling equipment, by electrically charging atomized water, Coulomb force causes increase in amount of adhesion to human skin, so that a cooling sensation can be increased.

In addition, according to the conventional electrostatic atomizing apparatus, water particles having an average particle diameter of 10 to 300 micrometers can be released, and, for example, at a building demolition site or the like, an electrically-charged water curtain composed of electrically-charged water particles is formed, dust floating in the air within a forming region of this electrically-charged water curtain are electrically absorbed and captured by the electrically-charged water particles, and the dust fall together with the electrically-charged water particles, so that the dust can be removed from the air.

The conventional electrically-charged water particle spraying apparatus is composed of a liquid conduit portion made of an insulation material for introducing pressurized water into an injection nozzle portion, the injection nozzle portion for jetting out water pressurized and fed from the liquid conduit portion to generate a mass of water particles, a ring-like induction electrode portion for forming a predetermined electric field when a predetermined voltage is applied to the induction electrode portion to inductively charge the mass of water particles generated at the injection nozzle portion with the electric field to generate a mass of electrically-charged water particles, and a water-side electrode portion for coming into contact with water to give a reference potential of the voltage applied to the induction electrode portion, and the induction electrode portion is retained, by an induction-electrode retaining arm structure provided with a plurality of retaining arms, in the vicinity of a region where the water jetted out from the injection nozzle portion is broken up into the water particles.

RELATED ART DOCUMENTS

Patent documents

Patent Document 1: Japanese Patent Application Laid-Open No. 2009-106405
Patent Document 2: Japanese Patent Application Laid-Open No. 2009-103335

SUMMARY OF THE INVENTION

Problems to be Solved by the Invention

Though such fine particles having an average particle diameter of 20 to 200 micrometers are electrically charged and released in the conventional electrostatic atomizing apparatus, some uses of the apparatus require an average particle diameter to be several micrometers or less, but it is difficult for the conventional electrostatic atomizing apparatus to electrically charge and release fine particles having an average particle diameter of several micrometers or less, and therefore this point remains a problem to be solved.

Furthermore, in the conventional electrically-charged water particle spraying apparatus, the induction electrode portion which applies a high voltage of several kilovolts in an environment where water spraying is handled has a conductive metal core material coated with a thick insulation material of from 100 micrometers to 6000 micrometers.

Moreover, the induction electrode portion must be positionally adjusted with the electrode retaining arms such that a ring center of a ring portion of the induction electrode portion coincides with a nozzle center of the injection nozzle, and, in order to prevent the position from shifting, a position where a constant pressing pressure is given is found and then the induction electrode portion is fixed there.

However, it is technically difficult to control a coating thickness of a thick insulation material of from 100 micrometers to 6000 micrometers accurately to a predetermined value even when the electrode core materials of the induction electrode portions having the same shapes and dimensions are coated, and therefore the coating thickness might differ in millimeters from one induction electrode portion to another induction electrode portion to be attached, so that the conventional induction electrode retaining arm structure requires difficult work of moving and adjusting the respective retaining positions of the retaining arms with respect to the apparatus body such that the ring-like induction electrode portion is aligned with the nozzle center and finding a position where a certain pressing pressure for retainment is applied. In this work, the presence of a distance between the injection nozzle and the induction electrode portion also causes difficulty in visual positioning and fixation.

Furthermore, if dirt or a flaw is found on the insulation coating material, the induction electrode portion is required to be replaced in order to maintain the insulating performance, and the replacement, conventionally, requires such troublesome work of detaching the entire electrically-charged water particle spraying apparatus from its installation place and then detaching the fixed retaining arms to replace the induction electrode portion.

An object of the present invention is to provide an electrostatic atomizing equipment capable of electrically charging and releasing fine particles having an average particle diameter of several micrometers or less.

In addition, another object of the present invention is to provide an electrically-charged water particle spraying apparatus simplifying and facilitating the work of retaining the ring center of the ring portion of the induction electrode portion so as to coincide with the nozzle center of the injection nozzle even when the outer diameter differs according to the coating of the insulation material.

Electrostatic Atomizing Apparatus

In an embodiment of the present invention, an electrostatic atomizing apparatus is provided with:
a liquid nozzle portion made of an insulation material for releasing a liquid column into an open space;
a liquid conduit portion made of an insulation material for introducing pressurized liquid into the liquid nozzle portion;
a liquid-side electrode for coming into contact with the liquid, the liquid-side electrode being disposed inside the liquid conduit portion or configured to be a portion of the liquid conduit portion and be made of a conductive material;
a gas conduit portion made of an insulation material and having a gas nozzle portion disposed around the liquid nozzle portion, for converting the liquid column into fine particles to generate an atomized stream which is a stream of gas containing the fine particles, by making a gas stream from the gas nozzle portion act at an atomization point which is a predetermined position of the liquid column released from the liquid nozzle portion into the open space; and
  a substantially ring-shaped induction electrode disposed around the atomization point located in the open space and having an electrode conductor made of a conductive material and coated with an insulation material, wherein
  the atomized stream of the fine particles electrically charged by applying a predetermined voltage between the liquid-side electrode and the induction electrode from a power supply portion is released.

Arrangement and Position of Induction Electrode

The induction electrode is in the open space, has a ring portion located outside the atomized stream expanding conically while having a ring center so located as to be on a common axis with the atomization point of the liquid nozzle portion and be nearer to the open space than the atomization point is, and, furthermore, is retained having a clearance for external air to flow in from an environment along with jetting out of the gas stream from the gas nozzle portion.

Liquid Pressure Attenuating Portion

In the electrostatic atomizing apparatus, a liquid pressure attenuating portion is further provided at a liquid-feeding side of the liquid conduit portion for reducing a pressure of a liquid fed and converting a flow velocity of the liquid fed into a uniform flow velocity, so that a formation state and a flow velocity of the liquid column released into the open space from the liquid nozzle portion is managed by pressure adjustment of the liquid fed.

Orifice Portion and Reflector Portion

The liquid pressure attenuating portion is provided with an orifice portion for restricting a flow rate of the liquid fed, and a reflector portion disposed at an outlet side of the orifice portion for reducing a pressure of a fluid and converting the flow velocity of the liquid fed into the uniform flow velocity.

Electrode Supply Voltage

The voltage applied between the liquid-side electrode and the induction electrode from the power supply portion is set in a range of +0.5 kV to +20 kV or −0.5 kV to −20 kV.

Not Grounding of Ground Cable

From the power supply portion, a voltage application cable is connected to the induction electrode and a ground cable is also connected to the liquid-side electrode, and the ground cable is not grounded but set at a floating potential in contrast to a ground potential.

Electrically-Charged Water Particle Spraying Apparatus

In addition, in another embodiment of the present invention, an electrically-charged water particle spraying apparatus is provided with:

an apparatus body;

a liquid conduit portion made of an insulation material for introducing pressurized water into an injection nozzle portion;

the injection nozzle portion for jetting out the water pressurized and fed from the liquid conduit portion to generate a mass of water particles;

a ring-shaped induction electrode portion for forming a predetermined electric field when a predetermined voltage is applied to the induction electrode portion, and using the electric field to inductively charge the mass of water particles generated by the injection nozzle portion to generate an electrically-charged mass of water particles;

a water-side electrode portion for coming into contact with the water to give a reference potential of the voltage applied to the induction electrode portion, the water-side electrode portion being disposed inside the liquid conduit portion or configured to be apart of the liquid conduit portion and be made of a conductive material; and an induction electrode retaining portion for retaining the induction electrode portion in a vicinity of a site where the water jetted out from the injection nozzle portion is broken up into the water particles, wherein the induction electrode portion is formed by coating a conductive electrode core material with an insulation material, the induction electrode retaining portion is provided with an induction electrode retaining arm having a leverage structure made of an insulation material for determining a retaining position of the induction electrode portion, and the induction electrode retaining arm includes at least three induction electrode retaining arms disposed at at least three locations, respectively, around a ring portion of the induction electrode portion, and a ring center of the ring portion is configured to be so retained as to coincide with a nozzle center of the injection nozzle portion, by making gripping portions serving as points of load of the leverage structures abut on the at least three locations on an outer peripheral portion of the ring portion to clamp the ring portion from three directions toward a center, making portions corresponding to fulcrums of the leverage structures abut on a body groove formed in the apparatus body, and applying a predetermined fastening force from a pressing portion through a plate simultaneously to all locations of points of effort of the leverage structures to apply a pressing force simultaneously to the gripping portions abutting on the outer peripheral portion of the ring portion.

Another Embodiment of Electrically-Charged Water Particle Spraying Apparatus

Furthermore, in another embodiment of the present invention, an electrically-charged water particle spraying apparatus is provided with:

an apparatus body;

a liquid conduit portion made of an insulation material for introducing pressurized water into an injection nozzle portion;

the injection nozzle portion for jetting out the water pressurized and fed from the liquid conduit portion to generate a mass of water particles;

a ring-shaped induction electrode portion for forming a predetermined electric field when a predetermined voltage is applied to the induction electrode portion, and using the electric field to inductively charge the mass of water particles generated by the injection nozzle portion to generate an electrically-charged mass of water particles;

a water-side electrode portion for coming into contact with the water to give a reference potential of the voltage applied to the induction electrode portion, the water-side electrode portion being disposed inside the liquid conduit portion or configured to be apart of the liquid conduit portion and be made of a conductive material; and an induction electrode retaining portion for retaining the induction electrode portion in a vicinity of a site where the water jetted out from the injection nozzle portion is broken up into the water particles, wherein the induction electrode portion is formed by coating a conductive electrode core material with an insulation material, the induction electrode retaining portion is provided with an induction electrode retaining arm made of an insulation material for determining a retaining portion of the induction electrode portion, and an induction electrode clamper for fixing the induction electrode portion in an electrode retaining position of the induction electrode retaining arm, such that the induction electrode retaining arm includes at least three induction electrode retaining arms for supporting a ring portion of the induction electrode portion at at least three locations, respectively, the induction electrode retaining arm is composed of a column portion and an arm portion, a groove for fitting the ring portion of the induction electrode portion by fixation of the induction electrode clamper is formed in an electrode retaining portion of the arm portion, a hole for attachment to a main body is provided in the column portion, and a threaded hole for fixing the induction electrode clamper is provided in the arm portion, and a ring center of the ring portion is configured to be so retained as to coincide with a nozzle center of the injection nozzle portion, by fitting the ring portion of the induction electrode portion put on the electrode retaining position of the arm portion into the groove formed by fixing the induction electrode clamper by fastening a screw inserted in the threaded hole to the arm portion.

Advantageous Effect of Electrostatic Atomizing Apparatus

According to the electrostatic atomizing apparatus of the present invention, an electrostatic atomizing apparatus is provided with: a liquid nozzle portion made of an insulation material for releasing a liquid column into an open space; a liquid conduit portion made of an insulation material for introducing pressurized liquid into the liquid nozzle portion; a liquid-side electrode for coming into contact with the liquid, the liquid-side electrode being disposed inside the liquid conduit portion or configured to be a portion of the liquid conduit portion and be made of a conductive material; a gas conduit portion made of an insulation material and having a gas nozzle portion disposed around the liquid nozzle portion, for converting the liquid column into fine particles to generate an atomized stream which is a stream of gas containing the fine particles, by making a gas stream from the gas nozzle portion act at an atomization point which is a predetermined position of the liquid column released from the liquid nozzle portion into the open space; and a substantially ring-shaped induction electrode disposed around the atomization point located in the open space and having an electrode conductor made of a conductive material and coated with an insulation material, wherein the atomized stream of the fine particles electrically charged by applying a predetermined voltage between the liquid-side electrode and the induction electrode from a power supply is released. Therefore, the gas stream generated by the gas nozzle portion is made to act on the liquid column released from the liquid nozzle portion to convert the liquid column into fine particles to generate an atomized stream which is a stream of gas containing the fine particles having an average particle diameter of several micrometers or less, and the predetermined voltage is applied between the liquid-side electrode and the induction electrode, so that the fine particles of the atomized stream can be electrically charged and released, and therefore the electrically-charged fine particles having an average particle diameter of several micrometers or less from liquid such as water or a chemical solution exert Coulomb force to adhere to an appropriate target efficiently so that an effect such as fire extinction or cooling resulting from the adhesion of the fine particles can be significantly increased, or an amount of absorption of dust or odor-causing substance in an atomization space can be increased.

Advantageous Effect of Arrangement and Position of Induction Electrode

In addition, since the induction electrode is in the open space, has a ring portion located outside the atomized stream expanding conically while having a ring center so located as to be on a common axis with the atomization point of the liquid nozzle portion and be nearer to the open space than the atomization point is, and, furthermore, is retained having a clearance for external air to flow in from an environment along with jetting out of the gas stream from the gas nozzle portion, this arrangement of the induction electrode causes a specific charge of the electrically-charged fine particle generated to be 1.0 mC/kg or more, and it has been confirmed that an electrically-charged fine particle of several micrometers or less can reliably be generated with this large specific charge.

Advantageous Effect of Liquid Pressure Attenuating Portion

In addition, in the electrostatic atomizing apparatus, a liquid pressure attenuating portion is further provided at a liquid-feeding side of the liquid conduit portion for reducing a pressure of a liquid fed and converting a flow velocity of the liquid fed into a uniform flow velocity, so that a formation state and a flow velocity of the liquid column released into the open space from the liquid nozzle portion is managed by pressure adjustment of the liquid fed, and the liquid pressure attenuating portion is provided with an orifice portion for restricting a flow rate of the liquid fed, and a reflector portion disposed at an outlet side of the orifice portion for reducing a pressure of a fluid and converting the flow velocity of the liquid fed into the uniform flow velocity. Therefore, the liquid column is stably and continuously released from the liquid nozzle portion, so that fine particles of several micrometers or less can reliably be generated by striking the gas stream from the gas nozzle portion into the liquid column, and can also be electrically charged and released.

In addition, since the pressure of the liquid fed to the liquid conduit portion is adjusted, an amount of atomization of the electrically charged fine particles can appropriately be adjusted, if necessary.

Advantageous Effect of Electrode Supply Voltage

In addition, since the voltage applied between the liquid-side electrode and the induction electrode from the power supply is set in a range of +0.5 kV to +20 kV or −0.5 kV to −20 kV, a spark discharge can be prevented from occurring.

Advantageous Effect of Not Grounding of Ground Cable

In addition, since from the power supply portion, a voltage application cable is connected to the induction electrode and a ground cable is also connected to the liquid-side electrode, and the ground cable is not grounded but set at a floating potential in contrast to a ground potential, even while high voltage is being applied from the power supply portion, a short-circuit current does not flow unless a user touches both the induction electrode and the liquid-side electrode simultaneously, and such a situation where a user touches both the induction electrode and the liquid-side electrode simultaneously can hardly be imagined, so that, consequently, higher safety can be ensured as compared with a case where the ground cable is so grounded as to be at a ground potential.

Advantageous Effect of Electrostatic Atomizing Apparatus According to Another Embodiment of the Present Invention In addition, according to another embodiment of the present invention, in an electrostatic atomizing apparatus, an electrically-charged water particle spraying apparatus is provided with: an apparatus body; a liquid conduit portion made of an insulation material for introducing pressurized water into an injection nozzle portion; the injection nozzle portion for jetting out the water pressurized and fed from the liquid conduit portion to generate a mass of water particles; a ring-shaped induction electrode portion for forming a predetermined electric field when a predetermined voltage is applied to the induction electrode portion, and using the electric field to inductively charge the mass of water particles generated by the injection nozzle portion to generate an electrically-charged mass of water particles; a water-side electrode portion for coming into contact with the water to give a reference potential of the voltage applied to the induction electrode portion, the water-side electrode portion being disposed inside the liquid conduit portion or configured to be a part of the liquid conduit portion and be made of a conductive material; and an induction electrode retaining portion for retaining the induction electrode portion in a vicinity of a site where the water jetted out from the injection nozzle portion is broken up into the water particles, wherein the induction electrode portion is formed by coating a conductive electrode core material with an insulation material, the induction electrode retaining portion is provided with an induction electrode retaining arm having a leverage structure made of an insulation material for determining a retaining position of the induction electrode portion, and the induction electrode retaining arm includes at least three induction electrode retaining arms disposed at at least three locations, respectively, around a ring portion of the induction electrode portion, and a center axis of the ring portion is configured to be so retained as to coincide with a center axis of the injection nozzle portion, by making gripping portions serving as points of load of the leverage structures abut on the at least three locations on an outer peripheral portion of the ring portion to clamp the ring portion from three directions toward a center, making portions corresponding to fulcrums of the leverage structures abut on a body groove formed in the apparatus body, and applying a predetermined fastening force from a pressing portion through a plate simultaneously to all locations of points of effort of the leverage structures to apply a pressing force simultaneously to the gripping portions abutting on the outer peripheral portion of the ring portion. Therefore, even when a coating thickness of the ring portion of the induction electrode portion is different from one induction electrode portion to another induction electrode portion, by applying a pressing force due to concentric circular displacement toward a ring center of the ring portion to the gripping portions abutting on the outer peripheral portion of the induction electrode portion, the center axis of the ring portion of the induction electrode portion can be so retained as to coincide with the center axis of the injection nozzle portion automatically, so that, in assembly work or in cleaning or replacement of the induction electrode portion, attachment and detachment of the induction electrode retaining arm and an electrode clamper for the induction electrode portion can be performed by work from a space near the induction electrode portion, and centering of the induction electrode portion is also eliminated or facilitated and ensured, and therefore the ring portion of the induction electrode portion can always be retained in a correct position with respect to a jet stream from the injection nozzle portion, regardless of the skill of a worker, so that good electrically-charging performance can always be achieved.

Advantageous Effect of Electrostatic Atomizing Apparatus According to Still Another Embodiment of the Present Invention In addition, according to another embodiment of the present invention, in an electrostatic atomizing apparatus, an electrically-charged water particle spraying apparatus is provided with: an apparatus body; a liquid conduit portion made of an insulation material for introducing pressurized water into an injection nozzle portion; the injection nozzle portion for jetting out the water pressurized and fed from the liquid conduit portion to generate a mass of water particles; a ring-shaped induction electrode portion for forming a predetermined electric field when a predetermined voltage is applied to the induction electrode portion, and using the electric field to inductively charge the mass of water particles generated by the injection nozzle portion to generate an electrically-charged mass of water particles; a water-side electrode portion for coming into contact with the water to give a reference potential of the voltage applied to the induction electrode portion, the water-side electrode portion being disposed inside the liquid conduit portion or configured to be a part of the liquid conduit portion and be made of a conductive material; and an induction electrode retaining portion for retaining the induction electrode portion in a vicinity of a site where the water jetted out from the injection nozzle portion is broken up into the water particles, wherein the induction electrode portion is formed by coating a conductive electrode core material with an insulation material, the induction electrode retaining portion is provided with an induction electrode retaining arm made of an insulation material for determining a retaining portion of the induction electrode portion, and an induction electrode clamper for fixing the induction electrode portion in an electrode retaining position of the induction electrode retaining arm, such that the induction electrode retaining arm includes at least three induction electrode retaining arms for supporting a ring portion of the induction electrode portion at at least three locations, respectively, the induction electrode retaining arm is composed of a column portion and an arm portion, a groove for fitting the ring portion of the induction electrode portion by fixation of the induction electrode clamper is formed in an electrode retaining portion of the arm portion, a hole for attachment to a main body is provided in the column portion, and a threaded hole for fixing the induction electrode clamper is provided in the arm portion, and a ring center of the ring portion is configured to be so retained as to coincide with a nozzle center of the injection nozzle portion, by fitting the ring portion of the induction electrode portion put on the electrode retaining position of the arm portion into the groove formed by fixing the induction electrode clamper by fastening a screw inserted in the threaded hole to the arm portion. Therefore, the groove for fitting the ring portion of the induction electrode portion by fixation of the induction electrode clamper is formed in the electrode retaining position of the arm portion of the induction electrode retaining portion, and, since the center diameter of the ring portion is not affected by the thickness of the insulation coating, the groove formed by fixation of the induction electrode clamper to the induction electrode retaining arm becomes a groove including the center diameter of the ring portion, and, since a surface shape of the coating is adapted to the position of the groove as long as the position of the groove is along the center diameter of the ring portion, regardless of the coating thickness of the induction electrode portion, the induction electrode portion can be retained in a predetermined position only by placing the induction electrode portion in the electrode retaining position without adjustment with respect to the induction electrode retaining arm, and directly fitting the induction electrode portion into the groove formed by fixation with the induction electrode clamper, so that, in assembly work or in cleaning or replacement of the induction electrode portion, attachment and detachment of the induction electrode retaining arm and the induction electrode clamper for the induction electrode portion can be performed by work from a space near the induction electrode portion, and centering of the induction electrode portion is also facilitated and ensured, and therefore the ring portion of the induction electrode portion can always be retained in a correct position with respect to a jet stream from the injection nozzle portion, regardless of the skill of a worker, so that good electrically-charging performance can always be achieved.

DETAILED DESCRIPTION OF THE INVENTION

Embodiment of Electrostatic Atomizing Apparatus

Figure 1:
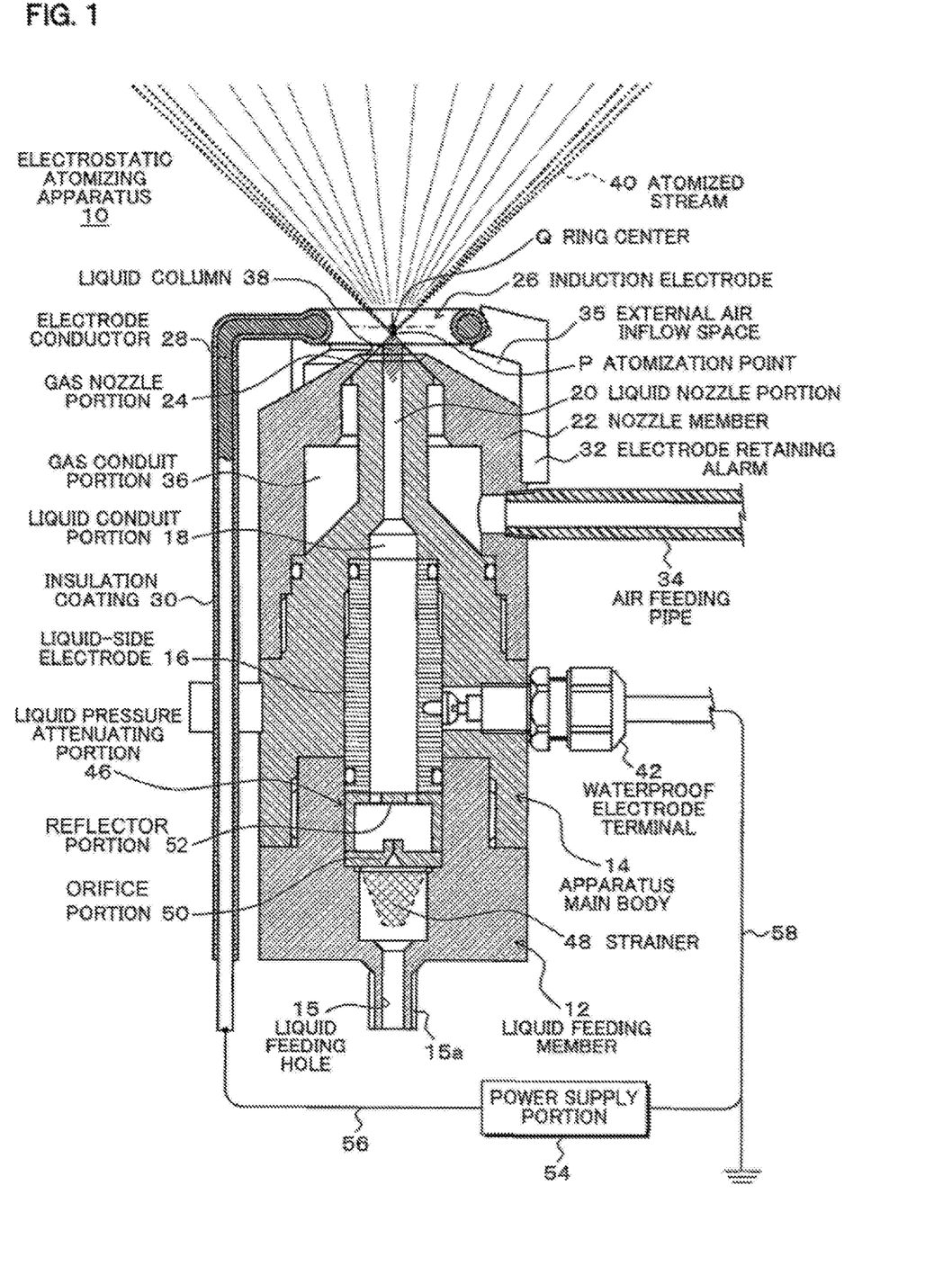
FIG. 1 is an illustrative view showing in cross section an embodiment of an electrostatic atomizing apparatus according to the present invention.
Figure 2:
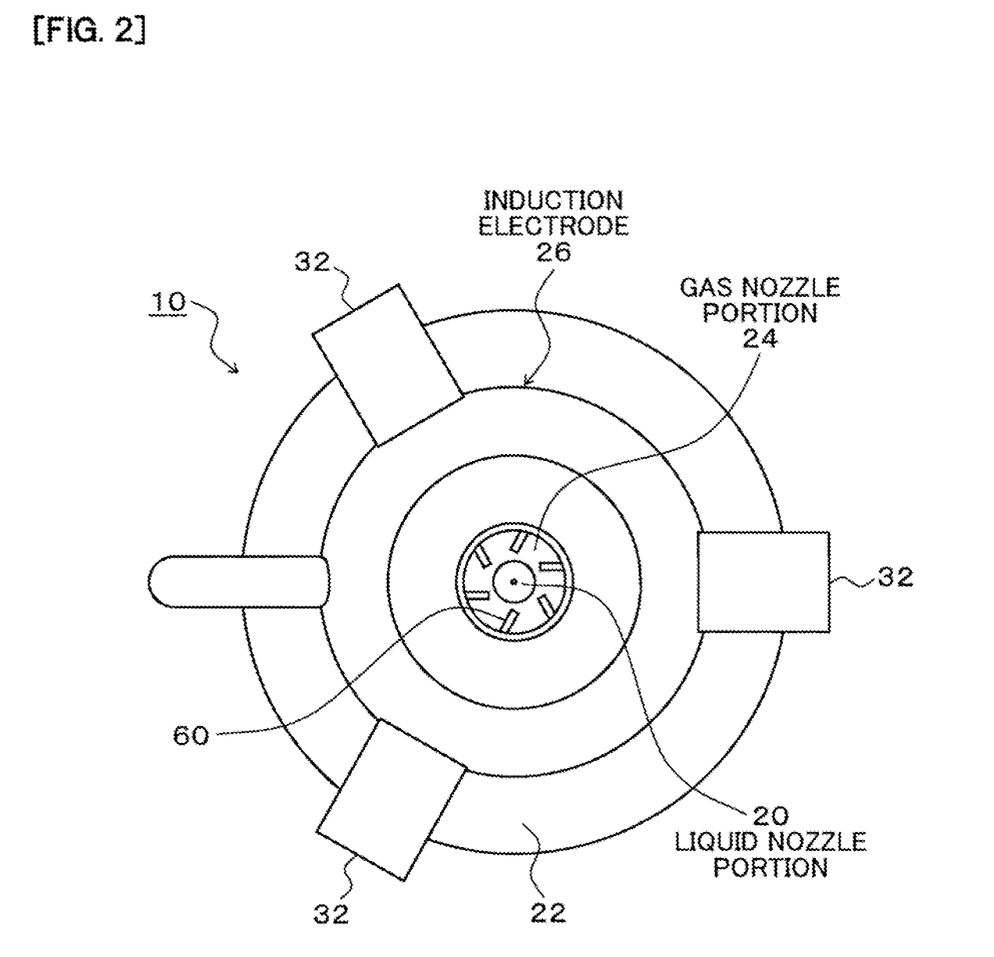
FIG. 2 is a top view showing the electrostatic atomizing apparatus of FIG. 1 as viewed from a releasing side.
Figure 3A:
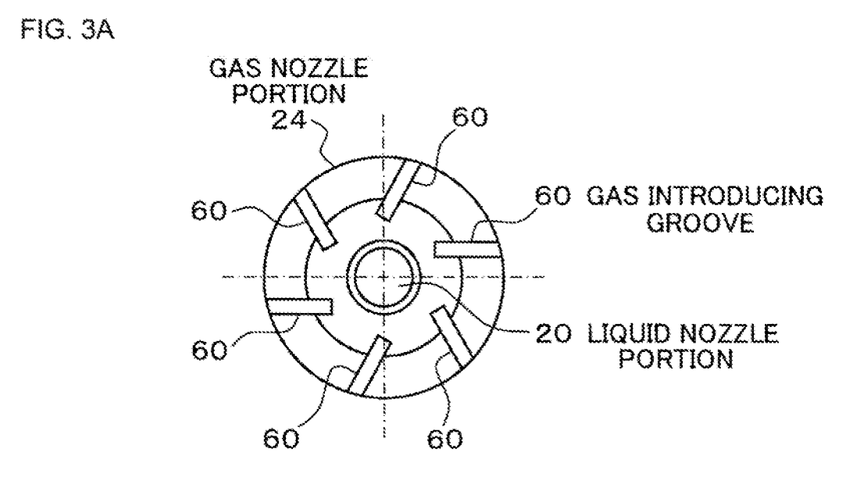
FIG. 3A and 3B are illustrative views picking out and showing a gas nozzle portion side of a liquid conduit portion provided in the electrostatic atomizing apparatus of FIG. 1.
Figure 3B:
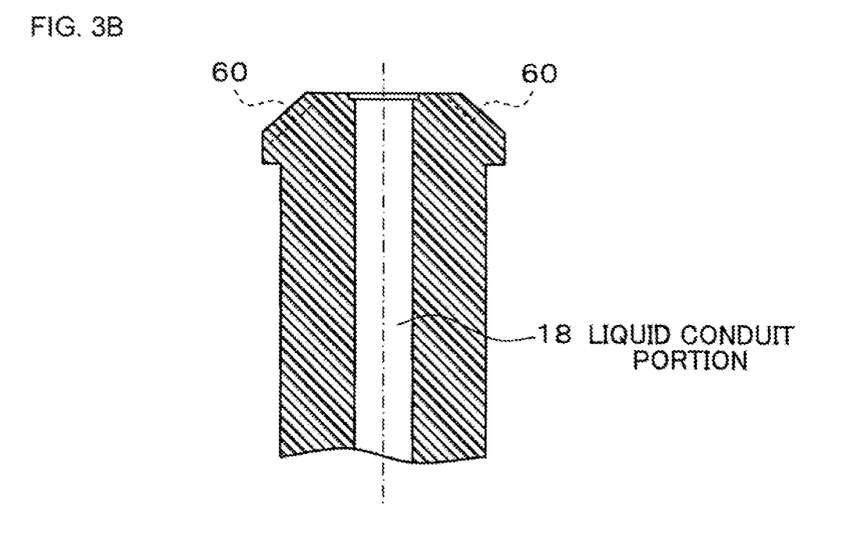

FIG. 1 is an illustrative view showing in cross section an embodiment of an electrostatic atomizing apparatus according to the present invention, FIG. 2 is a top view showing the electrostatic atomizing apparatus of FIG. 1 as viewed from a releasing side, and FIG. 3A and 3B are illustrative views picking out and showing a gas nozzle portion side of a liquid conduit portion provided in the electrostatic atomizing apparatus of FIG. 1, wherein FIG. 3A shows a plane as viewed from a nozzle opening side, and FIG. 3B shows an axial cross section.

Structure of Electrostatic Atomizing Apparatus

As shown in FIG. 1, an electrostatic atomizing apparatus 10 is composed of a liquid feeding member 12, an apparatus main body 14, and a nozzle member 22, and the liquid feeding member 12, the apparatus main body 14, and the nozzle member 22 are made of an insulation material. The insulating materials of the liquid feeding member 12, the apparatus main body 14, and the nozzle member 22 are formed by using as an insulation material at least one of polyvinyl chloride resin, polyphenylene sulfide resin, urethane resin, polytetrafluoroethylene resin, polychlorotrifluoroethylene resin, ceramic (alumina ceramic), and vitreous enamel.

A piping attachment threaded portion 15*a* is formed at an end portion of the liquid feeding member 12, a liquid feeding hole 15 is formed axially therein, and pressurized liquid such as water or chemicals pressurized by an external pump or the like is fed thereto. The pressure of the liquid fed to the liquid feeding member 12 is adjusted, for example, in a range of 0.1 to 1.0 MPa.

A liquid pressure attenuating portion 46 is provided in an internal flow channel communicating with the liquid feeding hole 15. A strainer 48, an orifice portion 50, and a reflector portion 52 are disposed in this order from an inflow side in the liquid pressure attenuating portion 46.

A liquid-side electrode 16 having a flow channel formed axially therein is incorporated inside the apparatus main body 14 provided following the liquid feeding member 12. The liquid-side electrode 16 is made of a metal conductive material.

Besides metal, the conductive material of the liquid-side electrode 16 may be formed by using resin, a fiber bundle, rubber, or the like, having electrical conductivity, or may be formed by using a composite body combining these materials.

A waterproof electrode terminal 42 is screwed and fixed to the liquid-side electrode 16 through a lateral attachment hole of the apparatus main body 14, with a distal end of the waterproof electrode terminal 42 fixed in electrical contact therewith.

At a distal end side of the apparatus main body 14, a shaft portion is formed following a conical tapering portion, a liquid conduit portion 18 is formed axially inside, and a liquid nozzle portion 20 is opened in a distal end of the liquid conduit portion 18.

The nozzle member 22 disposed outside the distal end of the apparatus main body 14 has a gas conduit portion 36 formed inside, has an air feeding pipe 34 joined and fixed to the gas conduit portion 36 from the right side in FIG. 1, and fed with air compressed to, for example, about 0.6 to 0.7 MPa from a compressor or the like through the air feeding pipe 34.

A gas nozzle portion 24 is formed at the distal ends of the nozzle member 22 and the apparatus main body 14. The gas nozzle portion 24 has a plurality of gas introducing groove portions 60 formed in spiral directions in an outer-peripheral tapering face of the liquid nozzle portion 20 opened in the distal end of the apparatus main body 14 shown in FIGS. 3A and 3B, and a tapered hole in the distal end of the nozzle member 22 is located outside the gas introducing groove portions 60, as shown in FIG. 1, to form the gas nozzle portion 24.

The gas nozzle portion 24 jets out air compressed through the gas introducing groove portions 60 spirally to a liquid column 38 released from the liquid nozzle portion 20 and, at an atomization point P which is a predetermined position of the liquid column 38 released into an open space from the liquid nozzle portion 20, a gas stream from the gas nozzle portion 24 is made to act to convert the liquid column 38 into fine particles to generate an atomized stream 40 which is a stream of gas containing the fine particles.

An induction electrode 26 is disposed in the open space near the distal ends of the liquid nozzle portion 20 and the gas nozzle portion 24. The induction electrode 26 has a distal ring portion disposed around the atomization point P located in the open space, an electrode conductor 28 made of a conductive material is coated with an insulation coating 30 made of an insulation material, and, as shown in FIG. 2, the ring portion is supported and fixed to the nozzle member 22 by three electrode retaining arms 32 disposed radially.

Here, the ring portion of the induction electrode 26 is located inside the open space near the distal end of the nozzle member 22, and located outside the atomized stream 40 expanding conically with a ring center Q so located as to be on a common axis with the atomization point P of the liquid column 38 and be nearer to the open space than (outside) the atomization point P of the liquid column 38 is, and furthermore the ring portion of the induction electrode 26 is retained with a clearance for forming an external air inflow space 35 into which external air flows from the environment along with jetting out of the gas stream from the gas nozzle portion 24.

The electrode conductor 28 of the induction electrode 26 is a conductive metal, but, besides metal, the electrode conductor 28 may be formed by using resin, a fiber bundle, rubber, or the like, having conductivity, or may be formed by using a composite body combining these materials.

In addition, the insulation material of insulation coating 30 of the induction electrode 26 is formed by using as an insulation material at least one of polyvinyl chloride resin, polyphenylene sulfide resin, urethane resin, polytetrafluoroethylene resin, polychlorotrifluoroethylene resin, ceramic (alumina ceramic), and vitreous enamel.

A voltage application cable 56 and aground cable 58 from a power supply portion 54 are connected to the liquid-side electrode 16 and the induction electrode 26, and the ground cable 58 to the liquid-side electrode 16 is grounded in this embodiment. When the power supply portion 54 applies a direct-current (alternating-current or pulsing) predetermined voltage in a range of +0.5 kV to +20 kV or −0.5 kV to −20 kV between the liquid-side electrode 16 and the induction electrode 26, a predetermined external electric field is formed around the ring portion of the induction electrode 26, the fine particles generated at the atomization point P are electrically charged, and the atomized stream 40 of the electrically-charged fine particles is released.

For example, if a direct-current voltage is applied to the induction electrode 26, the fine particles either positively charged or negatively charged are generated depending on the polarity of the induction electrode 26. Alternatively, if an alternating-current or pulsing voltage is applied, the fine particles positively charged or negatively charged selectively are generated depending on the polarity of the induction electrode 26 alternately switching.

Furthermore, the power supply portion 54 may maintain the voltage applied to the induction electrode 26 at a predetermined constant voltage in a range of [[+5]]+0.5 kV to +20 kV or [[−5]]−0.5 kV to −20 kV, or may change the voltage applied to the induction electrode 26 in a range of [[+5]]+0.5 kV to +20 kV or [[−5]]−0.5 kV to −20 kV. Moreover, by setting the applied voltage in the range of [[+5]]+0.5 kV to +20 kV or [[−5]]−0.5 kV to −20 kV in this manner, a spark discharge is prevented from occurring so that the atomized stream 40 of the electrically-charged fine particles can be generated with safety ensured.

Operation of Electrostatic Atomizing Apparatus

When the electrostatic atomizing apparatus 10 shown in FIG. 1 is used, the liquid pressurized by a pump or the like is fed through piping joined to the piping attachment threaded portion 15a, compressed air from a compressor or the like is also fed through the air feeding pipe 34, and furthermore a predetermined voltage in a range of +5 kV to +20 kV or −5 kV to −20 kV is applied between the liquid-side electrode 16 and the induction electrode 26 by the power supply portion 54.

The pressurized liquid fed from the liquid feeding hole 15 enters the reflector portion 52 from the strainer 48 while being restricted at the orifice portion 50 of the liquid pressure attenuating portion 46, a pressure of the pressurized liquid is reduced when the pressurized liquid passes through the orifice portion 50, and a flow velocity thereof is converted into a uniform flow velocity when the pressurized liquid passes through the reflector portion 52, and the pressurized liquid is then fed to the liquid nozzle portion 20 at the distal end through the liquid conduit portion 18 to release the liquid column 38 maintaining its cylindrical shape into the open space from the liquid nozzle portion 20.

Here, by adjusting the pressure of the pressurized liquid fed to the liquid feeding hole 15, a formation state and a flow rate (volume of release) of the liquid column 38 released from the liquid nozzle portion 20 can be adjusted and managed.

The pressurized air fed from the air feeding pipe 34 is fed to the gas nozzle portion 24 through the gas conduit portion 36, released into the open space through the spirally-arranged gas introducing groove portions 60 shown in FIG. 2 and FIGS. 3A and 3B, and hits to act on the liquid column 38 released from the liquid nozzle portion 20 at the atomization point P which is a predetermined position to convert the liquid column 38 into fine particles to generate the atomized stream 40 which is a stream of gas containing the fine particles having an average particle diameter of several micrometers or less.

The fine particles of the atomized stream 40 generated at the atomization point P are inductively charged by the external electric field formed at the ring portion of the induction electrode 26 to which a constant voltage has been applied, and the atomized stream 40 of a mass of the electrically-charged fine particles is released.

In a positional relationship between the atomization point P where the liquid column 38 is thus atomized by the action of the air stream and the ring center Q of the induction electrode 26, since the ring center Q is so located as to be on a common axis with the atomization point P of the liquid column 38 and be nearer to the open space than the atomization point P of the liquid column is, a specific charge of the fine particle electrically charged by the induction electric field of the induction electrode 26 becomes 1.0 to 20 mC/kg, and it has been confirmed that the electrically-charged fine particles can reliably be generated with such a large specific charge.

Illustrative Modification of Electrostatic Atomizing Apparatus

Liquid-Side Electrode

Though the liquid-side electrode made of a conductive material is disposed inside the liquid conduit portion in the above embodiment, the liquid-side electrode may be configured to be a portion of the liquid conduit portion made of an insulation material and be made of a conductive material.

Not Grounding of Ground Cable

Though the ground cable connected to the liquid-side electrode is grounded in the above embodiment, the ground cable may not be grounded but be at a floating potential floating from the ground. Since the ground cable is not grounded but at a floating potential, a short-circuit current does not flow unless a user touches both the induction electrode and the liquid-side electrode simultaneously, and such a situation where a user touches both the induction electrode and the liquid-side electrode simultaneously can hardly be imagined, so that higher security can consequently be ensured as compared with the case where the ground cable is so grounded as to be at a ground potential.

Others

The electrostatic atomizing apparatus of the present invention encompasses appropriate modifications without impairing the object and advantage thereof, and, furthermore, is not limited by numerical values presented in the above embodiment.

First Embodiment of Electrically-Charged Water Particle Spraying Apparatus

Figure 4A:
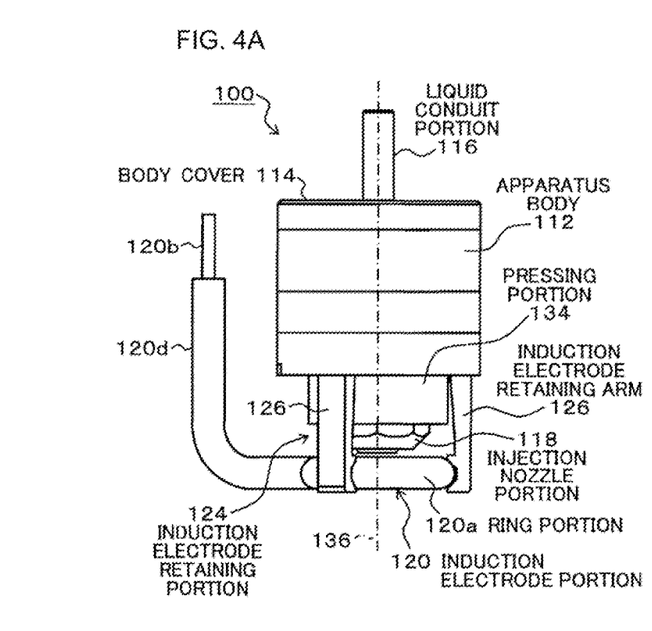
FIGS. 4A to 4D are illustrative views showing a first embodiment of an electrically-charged water particle spraying apparatus.
Figure 4B:
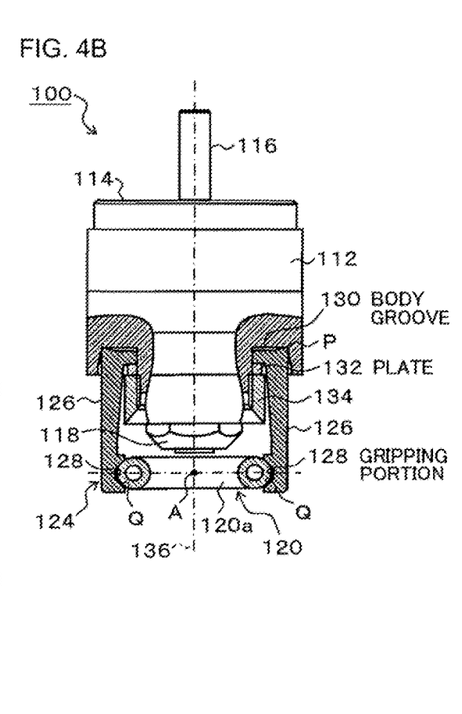
Figure 4C:
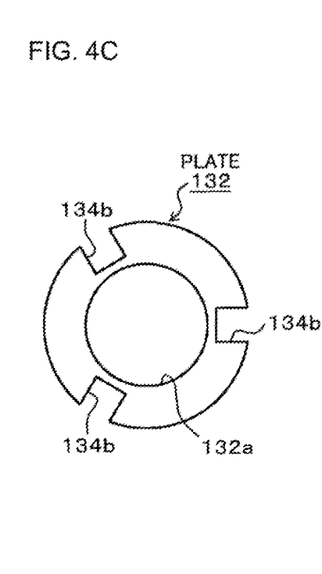
Figure 4D:
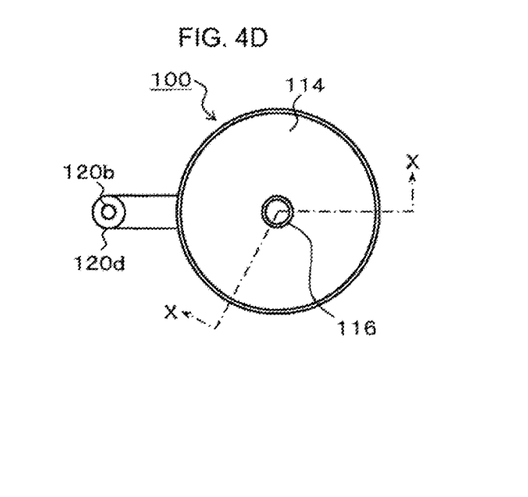
Figure 5:
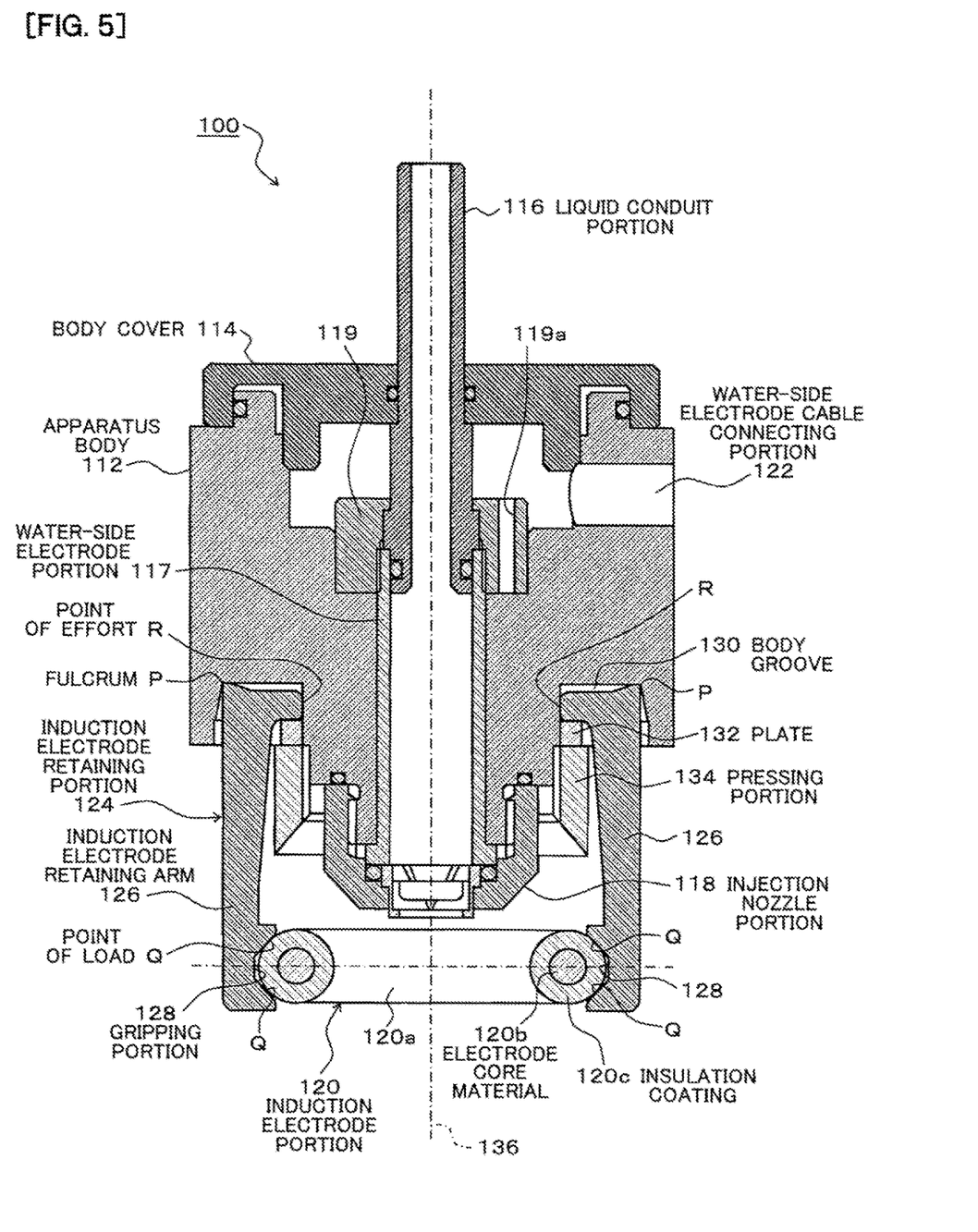
FIG. 5 is a cross-sectional view showing an internal structure of the electrically-charged water particle spraying apparatus of FIGS. 4A to 4D.

FIGS. 4A, 4B, 4C and 4D are illustrative views showing a first embodiment of an electrically-charged water particle spraying apparatus, wherein FIG. 4A shows a front face thereof, FIG. 4B shows a side face thereof partially cut away, FIG. 4C picks out and shows a plate, and FIG. 4D shows a top face thereof. FIG. 5 is a cross-sectional view showing an internal structure of the electrically-charged water particle spraying apparatus of FIGS. 4A to 4D, showing an X-X cross section of FIG. 4D. FIG. 6 is an illustrative view picking out and showing an induction electrode of the electrically-charged water particle spraying apparatus of FIGS. 4A and 4B.

Basic Structure

As shown in FIGS. 4A and 4B and FIG. 5, an electrically-charged water particle spraying apparatus 100 of this embodiment is composed of an apparatus body 112, a body cover 114, a liquid conduit portion 116, a water-side electrode portion 117, an injection nozzle portion 118, an induction electrode portion 120, and an induction electrode retaining portion 124.

The apparatus body 112, the body cover 114, the liquid conduit portion 116, the injection nozzle portion 118, and the induction electrode retaining portion 124 are made of an insulation material, and this insulation material is formed by using as an insulation material at least one of polyvinyl chloride resin, polyphenylene sulfide resin, urethane resin, polytetrafluoroethylene resin, polychlorotrifluoroethylene resin, ceramic (alumina ceramic), and vitreous enamel.

A through-hole is formed in the apparatus body 112 along a central axis 136, the water-side electrode 117 is fitted thereinto from below, the liquid-conduit portion 116 is fitted on an upper side of the water-side electrode 117, and an electrode coupling portion 119 is connected to the water-side electrode 117. A threaded hole 119a is provided in the electrode coupling portion 119, and a ground cable inserted through a water-side electrode cable connection hole 122 formed laterally in the apparatus body 112 is connected thereto. In addition, an upper portion of the liquid conduit portion 116 protrudes outside through the body cover 114, and water pressurized by an external pump or the like is fed thereto. The pressure of water fed to the liquid conduit portion 116 is adjusted in a range of, for example, 0.1 to 1.0 MPa.

The water-side electrode portion 117 and the electrode coupling portion 119 are made of a metal conductive material. Besides metal, the conductive material of the water-side electrode portion 117 and the electrode coupling portion 119 may be formed by using resin, a fiber bundle, rubber, or the like, having electrical conductivity, or may be formed by using a composite body combing these materials.

An injection nozzle portion 118 is provided on a distal end side of the water-side electrode portion 117 disposed axially in the apparatus body 112. The injection nozzle portion 118 releases water particles of an average particle diameter of 10 to 300 micrometers, and, for example, forms an electrically-charged water curtain composed of electrically-charged water particles at a building demolition site or the like, the electrically-charged water particles electrically absorb and capture dust floating in the air in a formation region of this electrically-charged water curtain, and the dust fall together with the electrically-charged water particles, so that the dust can be removed from the air.

In an open space on a distal end side of the injection nozzle portion 118, the induction electrode portion 120 is disposed with the induction electrode retaining portion 124. The induction electrode portion 120 is formed by coating a conductive electrode core material 120b with an insulation coating 120c, and has a ring-shaped ring portion 120a formed at a lower distal end of a supporting portion 120d disposed vertically, as picked out and shown in FIGS. 6A and 6B.

Figure 6A:
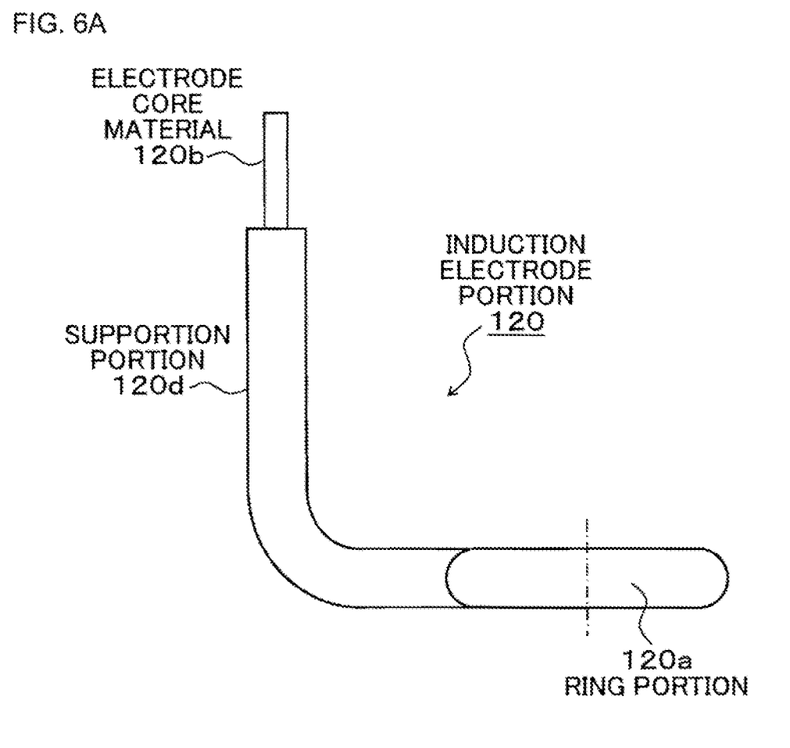
FIGS. 6A and 6B are illustrative views picking out and showing an induction electrode portion of the electrically-charged water particle spraying apparatus of FIGS. 4A to 4D.
Figure 6B:
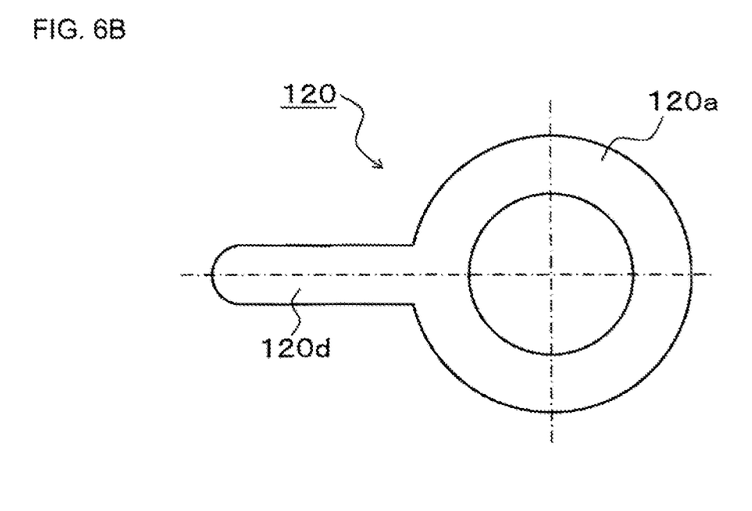

Though the electrode core material 120b of the induction electrode portion 120 is a conductive metal, but, besides metal, the electrode core material 120b may be formed by using resin, a fiber bundle, rubber, or the like, having conductivity, or may be formed by using a composite body combining these materials.

In addition, the insulation material of the insulation coating 120c of the induction electrode portion 120 is formed by using as an insulation material at least one of polyvinyl chloride resin, polyphenylene sulfide resin, urethane resin, polytetrafluoroethylene resin, polychlorotrifluoroethylene resin, ceramic (alumina ceramic), and vitreous enamel.

A ground cable and a voltage application cable are connected to the water-side electrode portion 117 and the induction electrode portion 120 from a power supply portion not shown, and, when a direct-current (alternating-current or pulsing) predetermined voltage in a range of +0.5 kV to +20 kV or −0.5 kV to −20 kV is applied between the water-side electrode portion 117 and the induction electrode portion 120, a predetermined external electric field is formed around the ring portion 120a of the induction electrode portion 120, and, because water jetted out from the injection nozzle portion 118 is broken up into water particles in the vicinity of a breakup point A, the water fine particles generated at the breakup point A are electrically charged, and an atomized stream of the electrically-charged water particles is released.

For example, if a direct-current voltage is applied to the induction electrode portion 120, the water particles either positively charged or negatively charged are generated depending on the polarity of the induction electrode portion 120. Alternatively, if an alternating-current or pulsing voltage is applied, the water particles positively charged or negatively charged selectively are generated depending on the polarity of the induction electrode portion 120 alternately switching.

Furthermore, the voltage applied to the induction electrode portion 120 by the power supply portion may be maintained at a constant voltage, or may be changed, in a range of +0.5 kV to +20 kV or −0.5 kV to −20 kV. Moreover, by setting the applied voltage in the range of +0.5 kV to +20 kV or −0.5 kV to −20 kV in this manner, a spark discharge is prevented from occurring so that the atomized stream of the electrically-charged water particles can be generated with safety ensured.

Retaining Structure of Induction Electrode Portion

As shown in FIGS. 4A and 4B and FIG. 5, the induction electrode retaining portion 124 is composed of a body groove 130 formed in a lower outer periphery of the apparatus body 112, three induction electrode retaining arms 126 for determining a retaining position of the induction electrode portion 120, a plate 132, and a pressing portion 134. The induction electrode retaining arms 126, the plate 132, and the pressing portion 134 are made of an insulation material, and this insulation material is formed by using as an insulation material at least one of polyvinyl chloride resin, polyphenylene sulfide resin, urethane resin, polytetrafluoroethylene resin, polychlorotrifluoroethylene resin, ceramic (alumina ceramic), and vitreous enamel.

The plate 132 has a ring hole 132a inside the ring plate, and has rectangular grooves 134b for fitting the induction electrode retaining arms 126 therein at three locations in an outer periphery, as picked out and shown in FIG. 4C.

When the induction electrode portion 120 is mounted on the apparatus body 112 with the induction electrode retaining portion 124, the induction electrode retaining arms 126 disposed in the rectangular grooves 134b of the plate 132 are fitted into an outer side of the injection nozzle portion 118 disposed at a lower portion of the body 112, and subsequently the pressing portion 134 is screwed in from below. In this state, with the ring portion 120a of the induction electrode portion 120 fitted in gripping portions 128 formed inside lower ends of the induction electrode retaining arms 126, the pressing portion 134 is screwed in to fix the induction electrode retaining arms 126 to the apparatus body 112 through the plate 132.

Here, the induction electrode retaining arms 126 have leverage structures for determining the retaining position of the induction electrode portion 120, by making the gripping portions 128 serving as points of load Q of the leverage structures abut on at least three locations in an outer peripheral portion of the ring portion 120a to clamp the ring portion 120a from three directions toward the center, making portions serving as fulcrums P of the leverage structures abut on the body groove 130, and applying predetermined fastening forces from the pressing portion 134 through the plate 132 simultaneously to all locations of points of effort R of the leverage structures to apply pressing forces simultaneously to the grip portions 128 abutting on the outer peripheral portion of the ring portion 120a, a ring center axis of the ring portion 120a automatically coincides with the nozzle center axis 136 of the injection nozzle portion 118, and is retained there.

Therefore, even when the coating thickness of the ring portion 120a of the induction electrode portion 120 is different from one induction electrode portion 120 to another induction electrode portion 120, by applying the pressing forces due to concentric circular displacement toward the ring center of the ring portion 120a to the gripping portions 128 abutting on the outer peripheral portion of the induction electrode portion 120, the center axis of the ring portion 120a of the induction electrode portion 120 can be so retained as to coincide with the central axis 136 of the injection nozzle portion 118 automatically, and therefore, in assembly work of the electrically-charged water particle spraying apparatus 100 or cleaning or replacement of the induction electrode portion 120, attachment and detachment of the induction electrode portion 120 can be performed by work from a space near the induction electrode portion 120, and centering of the induction electrode portion 120 is also eliminated or facilitated and ensured, so that the ring portion 120a of the induction electrode portion 120 can always be retained in a correct position with respect to a jet stream from the injection nozzle portion 118, regardless of the skill of a worker, and therefore good electrically-charging performance can always be achieved with respect to the atomized stream of the water particles injected from the injection nozzle portion 118.

Second Embodiment of Electrically-Charged Water Particle Spraying Apparatus

Figure 7A:
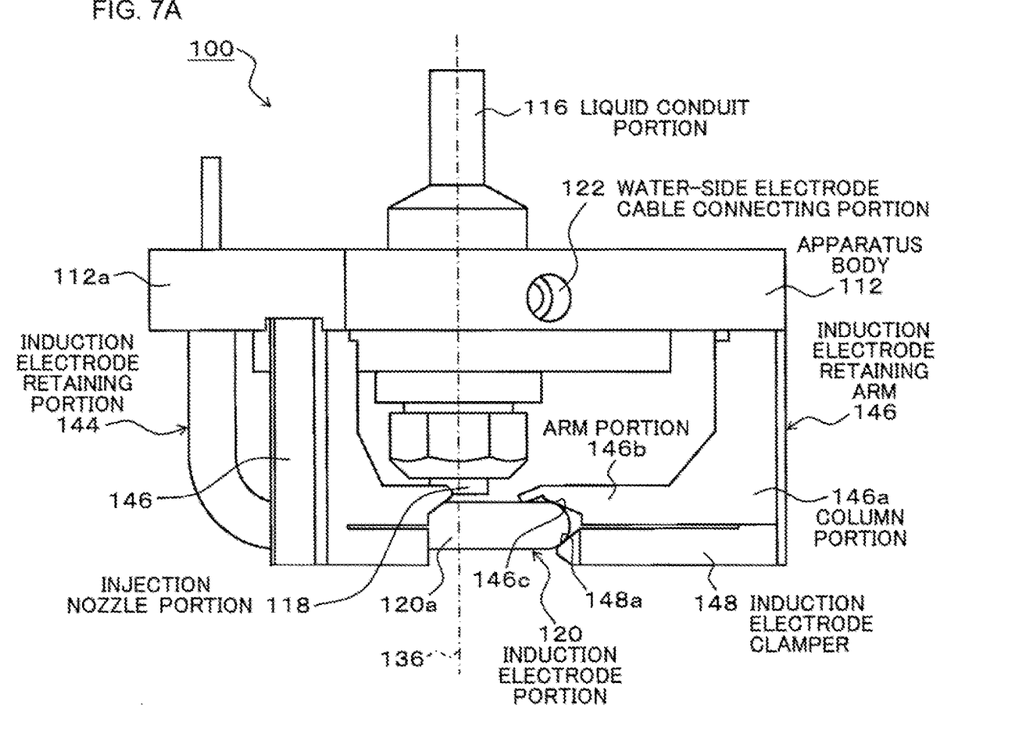
FIGS. 7A and 7B are illustrative views showing a second embodiment of the electrically-charged water particle spraying apparatus.
Figure 7B:
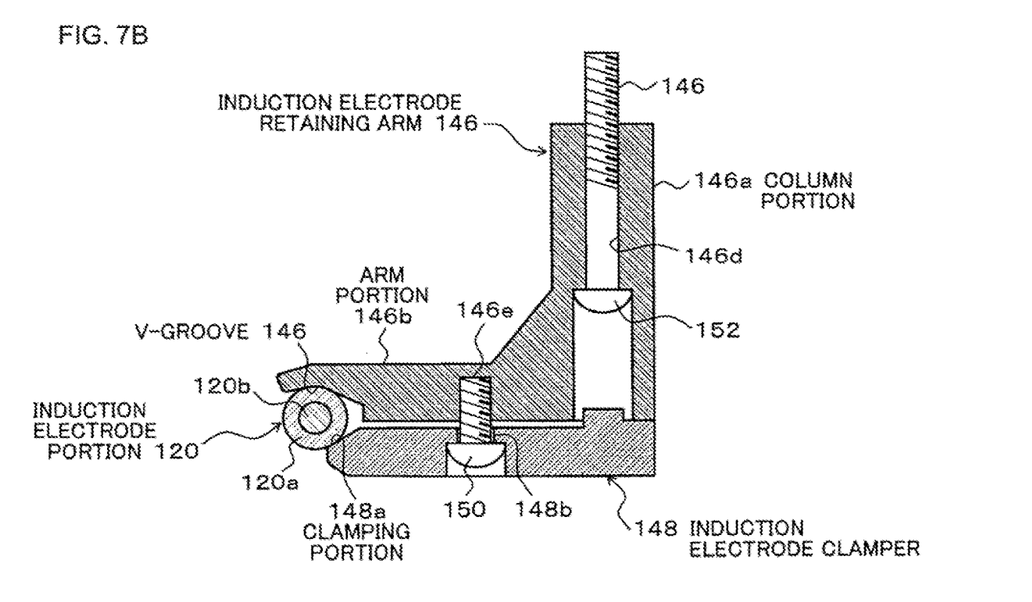

FIGS. 7A and 7B are illustrative views showing a second embodiment of the electrically-charged water particle spraying apparatus, wherein FIG. 7A shows an entire configuration thereof, and FIG. 7B picks out and shows an induction electrode retaining arm in cross section.

As shown in FIGS. 7A and 7B, the electrically-charged water particle spraying apparatus 100 of the second embodiment is composed of the apparatus body 112, the liquid conduit portion 116, the injection nozzle portion 118, the induction electrode portion 120, and an induction electrode retaining portion 144, and, except for the induction electrode retaining portion 144, the second embodiment is basically identical to the first embodiment shown in FIGS. 7A and 7B to FIG. 6, and therefore the descriptions thereof are omitted.

The induction electrode retaining portion 144 of the second embodiment is composed of three induction electrode retaining arms 146 for determining a retaining portion of the induction electrode portion 120 and induction electrode clampers 148 for fixing the induction electrode portion 120 in electrode retaining positions of the induction electrode retaining arms 146. The induction electrode retaining arms 146 and the induction electrode clampers 148 are made of an insulation material, and the insulation material is formed by using as an insulation material at least one of polyvinyl chloride resin, polyphenylene sulfide resin, urethane resin, polytetrafluoroethylene resin, polychlorotrifluoroethylene resin, ceramic (alumina ceramic), and vitreous enamel.

The induction electrode retaining arms 146 are so fixed as to be oriented downward at three locations in a flange portion 112a formed in an upper portion of the body 112, and so disposed as to support the ring portion 120a of the induction electrode portion 120 at at least three locations. The induction electrode retaining portion 144 is composed of a column portion 146a and an arm portion 146b, and a distal clamping portion 148a of the induction electrode camper 148 is disposed in the electrode retaining position of the arm portion 146b, and thereby a V-groove 146c including a center diameter of the ring portion 120a of the induction electrode portion 120 is formed, a through-hole 146d communicating with the apparatus body 112 is provided in the column portion 146a, and a threaded hole 146e for fixing the induction electrode clamper 148 is provided in the arm portion 146b.

When the induction electrode portion 120 is mounted on the apparatus body 112 with the induction electrode retaining portion 144, with the ring portion 120a of the induction electrode portion 120 put on the V-groove 146c of the arm portion 146b of the induction electrode retaining arm 146, the induction electrode clamper 148 is fixed by fastening a screw 150 inserted in a through-hole 148b to the arm portion 146b. Thereby, the ring center axis of the ring portion 120a of the induction electrode portion 120 coincides with the central axis 136 of the injection nozzle portion 118, and is retained there.

Therefore, since the V-groove 146c along the center diameter of the ring portion 120a of the induction electrode portion 120 is formed in the electrode retaining position of the arm portion 146b of the electrode retaining arm 146, and the center diameter of the ring portion 120a is not affected by the thickness of the insulation coating 120c, as long as the position of the V-groove 146c of the induction electrode retaining arm 146 is along the center diameter of the ring portion 120a, regardless of the coating thickness of the insulation coating 120c of the induction electrode portion 120, a surface shape of the coating is adapted to the position of the V-groove 146c, so that the induction electrode portion 120 can be retained in a predetermined position only by placing the induction electrode portion 120 on the V-grooves 146c of the arm portions 146b of the induction electrode retaining arms 146 without adjustment and fixing the induction electrode portion 120 directly with the induction electrode retaining arm clamper 148.

As a result, in assembly work of the electrically-charged water particle spraying apparatus 100 or cleaning or replacement of the induction electrode portion 120, attachment and detachment of the induction electrode retaining arm 146 and the induction electrode clamper 148 for the induction electrode portion 120 can be performed by work from a space near the induction electrode portion 120, and centering of the induction electrode portion 120 is also facilitated and ensured, so that the ring portion 120a of the induction electrode portion 120 can always be retained in a correct position with respect to a jet stream of water particles from the injection nozzle portion 118, regardless of the skill of a worker, and therefore good electrically-charging performance can always be achieved.

Illustrative Modification of Electrically-Charged Water Particle Spraying Apparatus Though the water-side electrode portion made of a conductive material is disposed inside the liquid conduit portion in the above embodiment, the water-side electrode portion may be configured to be a portion of the liquid conduit portion made of an insulation material and be made of a conductive material.

In addition, the electrically-charged water particle spraying apparatus of the present invention encompasses appropriate modifications without impairing the object and advantage thereof and, furthermore, is not limited by numerical values presented in the above embodiments.

DESCRIPTION OF REFERENCE NUMERALS

10: Electrostatic atomizing apparatus
12: Liquid feeding member
14: Apparatus main body
15: Liquid feeding hole
16: Liquid-side electrode
18: Liquid conduit portion
20: Liquid nozzle portion
22: Nozzle member
24: Gas nozzle portion
26: Induction electrode
28: Electrode conductor
30: Insulation coating
32: Electrode retaining arm
34: Air feeding pipe
36: Gas conduit portion
38: Liquid column
40: Atomized stream
42: Waterproof electrode terminal
46: Liquid pressure attenuating portion
48: Strainer
50: Orifice
52: Reflector portion 54: Power supply portion
56: Voltage application cable
58: Ground cable
60: Gas introducing groove portion
100: Electrically-charged water particle spraying apparatus
112: Apparatus body
114: Body cover
116: Liquid conduit portion
117: Water-side electrode portion
118: Injection nozzle portion
120: Induction electrode portion
120a: Ring portion
120b: Electrode core material
120c: Insulation coating
122: Water-side electrode cable connecting hole
124, 144: Induction electrode retaining portion
126, 146: Induction electrode retaining arm
128: Gripping portion
130: Body groove
132: Plate
134: Pressing portion
136: Central axis
146a: Column portion
146b: Arm portion
146c: V-groove
146d, 148b: Through-hole
148: Induction electrode clamper
150, 152: Screw

The invention claimed is:

1. An electrostatic atomizing apparatus comprising:
a liquid nozzle portion made of an insulation material for releasing a liquid column into an open space;
a liquid conduit portion made of an insulation material for introducing a pressurized liquid from a liquid-feeding hole into the liquid nozzle portion;
a liquid-side electrode for coming into contact with the pressurized liquid, the liquid-side electrode being disposed inside the liquid conduit portion or configured to be a portion of the liquid conduit portion and be made of a conductive material;
a gas conduit portion made of an insulation material and having a gas nozzle portion disposed around the liquid nozzle portion, for converting the liquid column into fine particles to generate an atomized stream which is a stream of gas containing the fine particles, by making a gas stream from the gas nozzle portion act at an atomization point which is a position of the liquid column released from the liquid nozzle portion into the open space;
a liquid pressure attenuating portion between the liquid-side electrode and the liquid-feeding hole for reducing a pressure of the pressurized liquid and converting a flow velocity of the pressurized liquid into a uniform flow velocity such that a formation state and a flow velocity of the liquid column released into the open space from the liquid nozzle portion is managed by pressure adjustment of the pressurized liquid; and
a ring-shaped induction electrode disposed around the atomization point located in the open space and having an electrode conductor made of a conductive material and coated with an insulation material,
wherein:
the liquid pressure attenuating portion is provided in a liquid-feeding member having the liquid-feeding hole, and comprises a strainer disposed at an outlet side of the liquid-feeding hole, an orifice portion disposed at an outlet side of the strainer for restricting a flow rate of the pressurized liquid, and a reflector portion disposed at an outlet side of the orifice portion for reducing the pressure of the pressurized liquid and converting the flow velocity of the pressurized liquid into the uniform flow velocity, in that order; and
the electrostatic atomizing apparatus is configured to electrically charge the atomized stream of the fine particles by applying a voltage between the liquid-side electrode and the ring-shaped induction electrode from a power supply portion, and release the atomized stream of the fine particles.

2. The electrostatic atomizing apparatus according to claim 1, wherein:
the ring-shaped induction electrode is in the open space, has a ring portion configured to be outside the atomized stream expanding conically while having a ring center located so as to be on a common axis with the atomization point and be nearer to the open space than the atomization point; and
the ring-shaped induction electrode is positioned so as to provide a clearance for external air to flow in from an environment along with jetting out of the gas stream from the gas nozzle portion.

3. The electrostatic atomizing apparatus according to claim 1, wherein the voltage is in a range of +0.5 kV to +20 kV or −0.5 kV to −20 kV.

4. The electrostatic atomizing apparatus according to claim 1, wherein, from the power supply portion, a voltage application cable is connected to the ring-shaped induction electrode, a ground cable is connected to the liquid-side electrode, and the ground cable is not grounded but is set at a floating potential in contrast to a ground potential.

* * * * *